United States Patent
Kodaira et al.

(10) Patent No.: US 12,005,621 B2
(45) Date of Patent: Jun. 11, 2024

(54) MANUFACTURING METHOD AND INJECTION MOLDING SYSTEM

(71) Applicant: Canon Virginia, Inc., Newport News, VA (US)

(72) Inventors: Koki Kodaira, Tokyo (JP); Yuichi Yanahara, Moriyama (JP)

(73) Assignee: Canon Virginia, Inc., Newport News, VA (US)

( * ) Notice: Subject to any disclaimer, the term of this patent is extended or adjusted under 35 U.S.C. 154(b) by 81 days.

(21) Appl. No.: 17/611,513

(22) PCT Filed: May 13, 2020

(86) PCT No.: PCT/US2020/032749
§ 371 (c)(1),
(2) Date: Nov. 15, 2021

(87) PCT Pub. No.: WO2020/236495
PCT Pub. Date: Nov. 26, 2020

(65) Prior Publication Data
US 2022/0203591 A1   Jun. 30, 2022

Related U.S. Application Data (60) Provisional application No. 62/849,739, filed on May 17, 2019.

(51) Int. Cl.
*B29C 45/76* (2006.01)
*A61L 31/04* (2006.01)
(Continued)

(52) U.S. Cl.
CPC ........ *B29C 45/7686* (2013.01); *A61L 31/041* (2013.01); *A61L 31/042* (2013.01);
(Continued)

(58) Field of Classification Search
CPC ............ B29C 45/7686; B29C 45/0408; B29C 2945/76464; B29C 2945/76973; B29C 2945/76976; B29C 45/76
See application file for complete search history.

(56) References Cited

U.S. PATENT DOCUMENTS 11,104,050  B2   8/2021   Nakamura
2006/0172039 A1  8/2006   Imai
(Continued)

FOREIGN PATENT DOCUMENTS

JP   2002225065 A  *  8/2002
JP   2007304011 A     11/2007
(Continued)

*Primary Examiner* — S. Behrooz Ghorishi
(74) *Attorney, Agent, or Firm* — Canon U.S.A., Inc., IP Division (57) ABSTRACT

A method for manufacturing a molded part while changing between multiple molds including a first ejecting step of opening a first mold and ejecting the molded part from the first mold, a checking step of checking the ejected molded part to determine if the molded part is acceptable, a first injecting step of closing the first mold and performing injection into the first mold, a second ejecting step of, where the ejected molded part is determined to be acceptable, changing the first mold to a second mold and ejecting the molded part from the second mold after the first injecting step, and a third ejecting step of, in a case where the molded part ejected in the first ejecting step is determined to be non-acceptable, not changing the first mold to the second mold and ejecting the molded part from the first mold.

13 Claims, 9 Drawing Sheets

(51) Int. Cl.
  *B29C 45/04*     (2006.01)
  *B29C 45/17*     (2006.01)
  *C08L 1/28*      (2006.01)
  *C08L 5/08*      (2006.01)

(52) U.S. Cl.
  CPC ...... *B29C 45/0408* (2013.01); *B29C 45/1756* (2013.01); *C08L 1/28* (2013.01); *C08L 5/08* (2013.01); *B29C 2945/76464* (2013.01); *B29C 2945/76973* (2013.01); *C08L 2203/02* (2013.01)

(56) References Cited

U.S. PATENT DOCUMENTS

2016/0311146 A1* 10/2016 Ichihara .............. B29C 45/1769
2017/0291343 A1* 10/2017 Uchiyama ............. G01N 21/88
2018/0009146 A1   1/2018 Nakamura

FOREIGN PATENT DOCUMENTS

| JP | 2009-083191 A |   | 4/2009 |
| JP | 2009083191 A  | * | 4/2009 |
| JP | 2016112771 A  |   | 6/2016 |
| JP | 6121601 B1    |   | 4/2017 |

* cited by examiner

MANUFACTURING METHOD AND INJECTION MOLDING SYSTEM

CROSS-REFERENCE TO RELATED APPLICATION

This application claims the benefit of U.S. Provisional Application 62/849,738, which was filed on May 17, 2019.

FIELD

The present disclosure relates to an injection molding system.

BACKGROUND

Manufacturing of molded parts by an injection molding machine includes injecting a resin into a mold after clamping the mold, pressing the resin into the mold at a high pressure in order to compensate for a volume decrease due to solidification of the resin, keeping the molded part in the mold until the resin solidifies, and ejecting the molded part from the mold.

Figure 1:
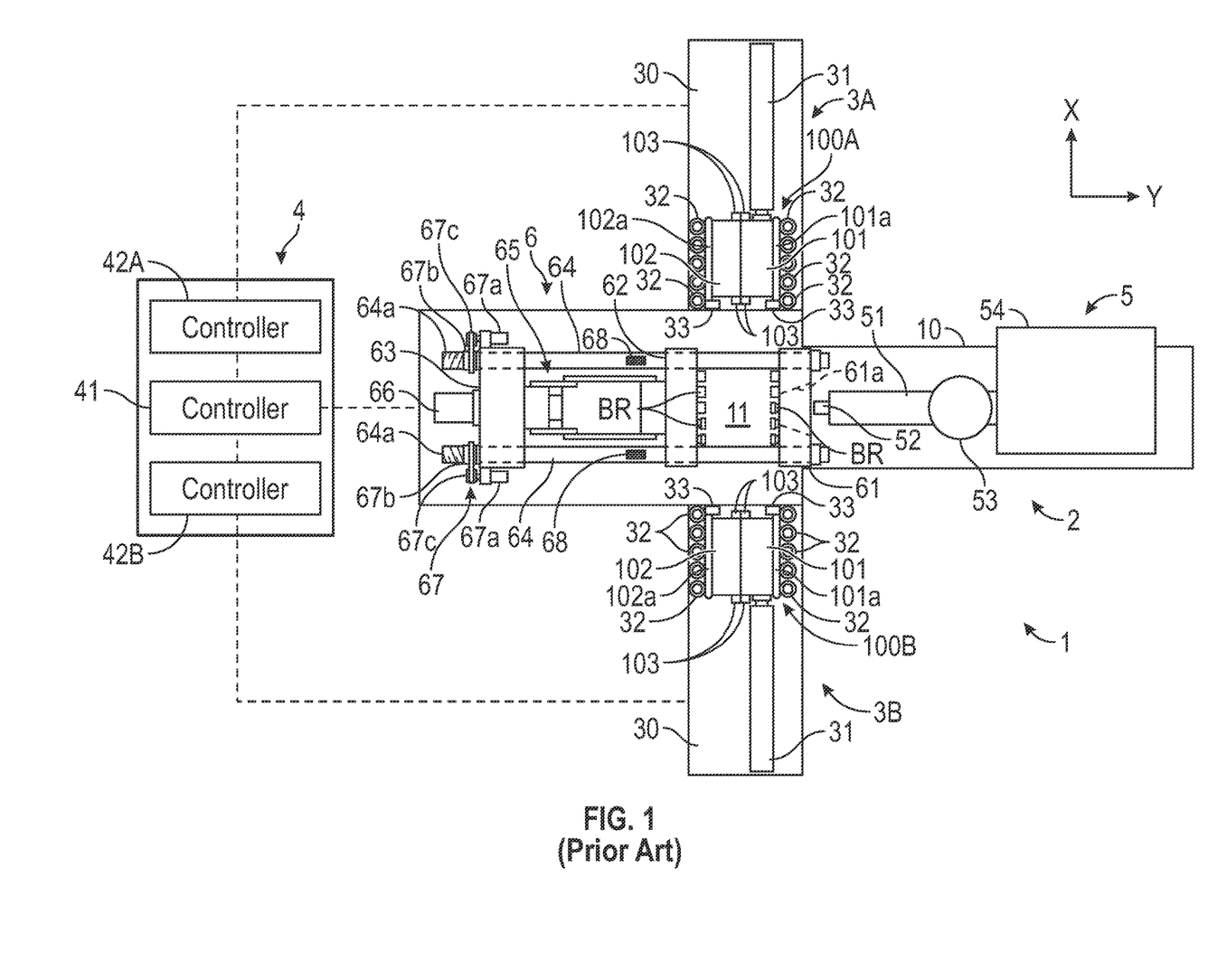
FIG. 1 illustrates an injection molding system.
Figure 2:
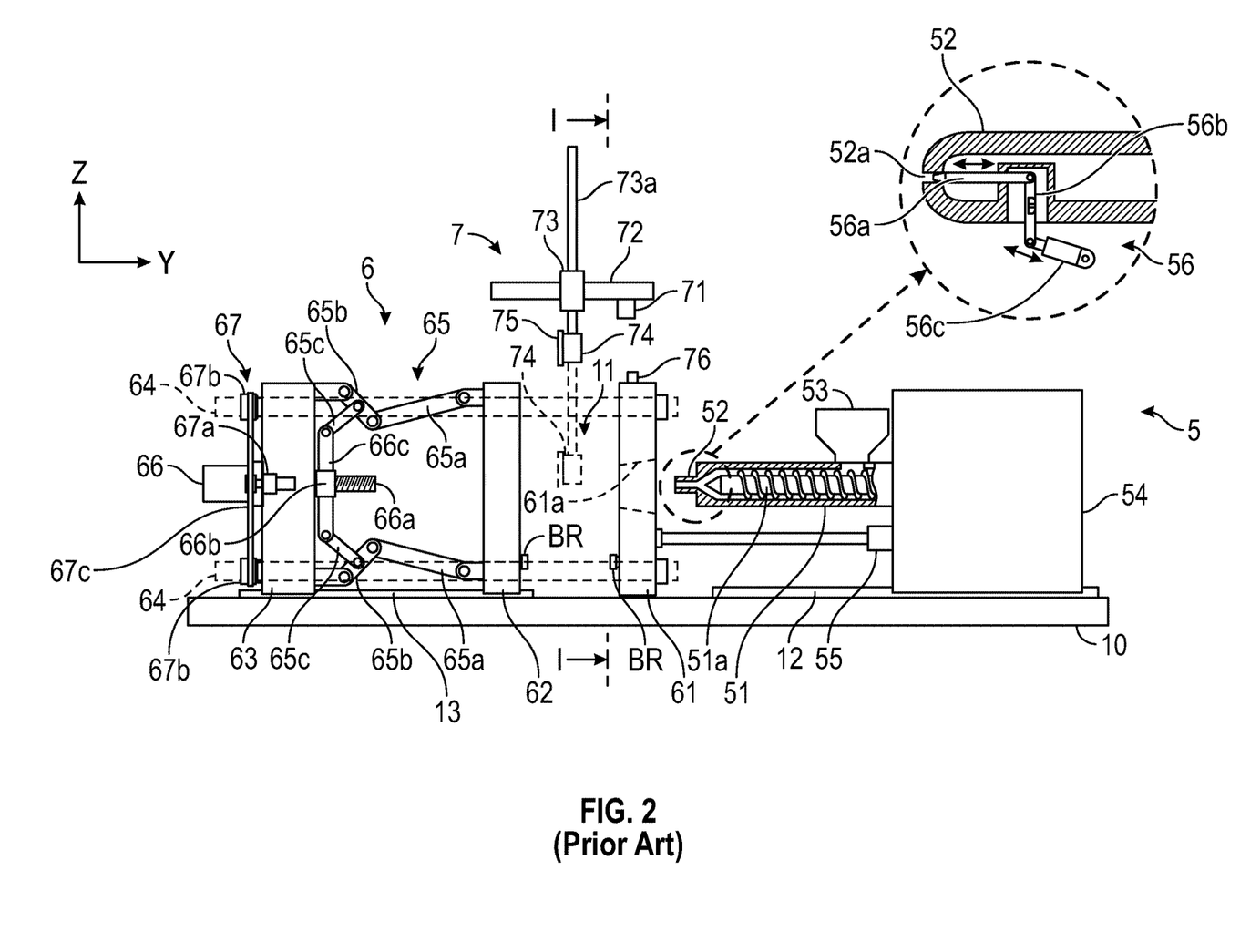
FIG. 2 illustrates a side view of an injection molding machine.

In the above-described molding approach, a method that uses two molds with one injection molding machine in order to enhance productivity has been proposed. For example, US 2018/0009146/Japanese patent publication No. 2018-001738/VN20160002505 are seen to discuss a system in which conveying devices 3A and 3B are arranged on both sides of an injection molding machine 2. In this system, molded parts are manufactured while alternating a plurality of molds by the conveying devices 3A and 3B for the one injection molding machine 2. FIGS. 1-2 illustrates an injection molding system of US 2018/0009146/Japanese patent publication No. 2018-001738/VN20160002505.

In this system, cooling of the molds 100A or 100B is performed on the conveying machines 3A or 3B outside of the injection molding machine 2. During cooling of one of the molds 100A/100B, each process of molded part ejection→clamping→injection/dwelling is performed by the injection molding machine 2 for the other mold 100A/100B. Since opening and molded part ejection are performed by the injection molding machine 2, the conveying machines 3A and 3B do not need a function for opening and a function for molded part ejection.

This enables manufacture of the molded part P while alternating the plurality of the molds by the one injection molding machine 2. This can reduce the overall cost of the system.

If the time required for all processes from the start of the mold replacement process, to the other mold ejecting process, injection process, and dwelling process, and up until completion of the mold replacement process once again fits into the time required for cooling one of the molds, then productivity compared to normal molding is improved by a maximum of two times. That is, in addition to suppressing cost increases, there is the merit that it is possible to realize high productivity.

A technique for heat and cool molding is known. In this technique, the mold is heated in advance to a temperature higher than the thermal deformation temperature of the resin, and after the resin is injected into the mold, the mold is cooled. While this technique can prevent appearance defects of molded parts, it requires an apparatus for forced heating and cooling. In addition, there is a disadvantage that the molding process is longer than that of a typical molding method.

A method for checking/inspecting molded parts is disclosed in Japanese patent publication No. 2007-304011. In this case, molded nuts are placed on a rotating table, a capturing unit captures an image of the molded nuts, and quality of the molded nuts is determined by analyzing the captured image.

What is needed is a technique for performing injection molding and inspecting molded parts while alternating multiple molds . . . .

SUMMARY

According to at least one aspect of the present disclosure, a method for manufacturing a molded part by an injection molding machine while changing between multiple molds, the method including a first ejecting step of opening a first mold in the injection molding machine and ejecting the molded part from the first mold, a checking step of checking the molded part, ejected in the first ejecting step, to determine if the molded part is an acceptable part, a first injecting step of closing the first mold and performing injection into the first mold, a second ejecting step of, in a case where the molded part ejected in the first ejecting step is determined to be an acceptable part, changing the first mold in the injection molding machine to a second mold and ejecting the molded part from the second mold after the first injecting step, and a third ejecting step of, in a case where the molded part ejected in the first ejecting step is determined to be a non-acceptable part, not changing the first mold to the second mold and ejecting the molded part from the first mold.

This and other embodiments, features, and advantages of the present disclosure will become apparent upon reading the following detailed description of exemplary embodiments of the present disclosure, when taken in conjunction with the appended drawings, and provided claims.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DESCRIPTION OF EXEMPLARY EMBODIMENTS

The present disclosure has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

With reference to the drawings, the arrow symbols X and Y in each Figure indicate horizontal directions that are orthogonal to each other, and the arrow symbol Z indicates a vertical (upright) direction with respect to the ground.

FIGS. 1-2 illustrate injection molding system 1 of US 2018/0009146/Japanese patent publication No. 2018-001738/VN20160002505 and are being provided herein for information/description purposes only.

The injection molding system 1 includes an injection molding machine 2, conveying machines 3A and 3B, and a control apparatus 4. The injection molding system 1 manufactures a molded part while alternating a plurality of molds using the conveying machines 3A and 3B for the one injection molding machine 2. Two molds, 100A and 100B are used.

The mold 100A/100B is a pair of a fixed mold 101 and a movable mold 102, which is opened/closed in relation to the fixed mold 101. The molded part is molded by injecting a molten resin into a cavity formed between the fixed mold 101 and the movable mold 102. Clamping plates 101a and 102a are respectively fixed to the fixed mold 101 and the movable mold 102. The clamping plates 101a and 102a are used to lock the mold 100A/100B to a molding operation position 11 (mold clamping position) of the injection molding machine.

For the mold 100A/100B, a self-closing unit 103 is provided for maintaining a closed state between the fixed mold 101 and the movable mold 102. The self-closing unit 103 enables preventing the mold 100A/100B from opening after unloading the mold 100A/100B from the injection molding machine 2. The self-closing unit 103 maintains the mold 100A/100B in a closed state using a magnetic force. The self-closing unit 103 located at a plurality of locations along opposing surfaces of the fixed mold 101 and the movable mold 102. The self-closing unit 103 is a combination of an element on the side of the fixed mold 101 and an element on the side of the movable mold 102. For the self-closing unit 103, typically two or more pair are installed for one of the molds 100A and 100B.

A conveying machine 3A loads and unloads the mold 100A onto/from the molding operation position 11 of the injection molding machine 2. A conveying machine 3B loads and unloads the mold 100B onto/from the molding operation position 11. The conveying machine 3A, the injection molding machine 2, and the conveying machine 3B are arranged to be lined up in this order in the X-axis direction. In other words, the conveying machine 3A and the conveying machine 3B are arranged laterally with respect to the injection molding machine 2 to sandwich the injection molding machine 2 in the X-axis direction. The conveying machines 3A and 3B are arranged to face each other, and the conveying machine 3A is arranged on one side laterally of the injection molding machine 2, and the conveying machine 3B is arranged on the other side respectively adjacent. The molding operation position 11 is positioned between the conveying machine 3A and the conveying machine 3B. The conveying machines 3A and 3B respectively include a frame 30, a conveyance unit 31, a plurality of rollers 32, and a plurality of rollers 33.

The frame 30 is a skeleton of the conveying machine 3A and 3B, and supports the conveyance unit 31, and the pluralities of rollers 32 and 33. The conveyance unit 31 is an apparatus that moves the mold 100A/100B back and forth in the X-axis direction, and that removes and inserts the mold 100A/100B in relation to the molding operation position 11.

The conveyance unit 31 is an electrically driven cylinder with a motor as a driving source, and includes a rod that moves forward/backward in relation to the cylinder. The cylinder is fixed to the frame 30, and the fixed mold 101 is fixed to the edge portion of the rod. For the conveyance unit 31 both a fluid actuator and an electric actuator can be used, where the electric actuator can provide better precision of control of the position or the speed when conveying the mold 100A/100B. The fluid actuator can be an oil hydraulic cylinder, or an air cylinder, for example. The electric actuator can, in addition to an electrically driven cylinder, be a rack-and-pinion mechanism with a motor as the driving source, a ball screw mechanism with a motor as the driving source, or the like.

The conveyance unit 31 is arranged independently for each of the conveying machines 3A and 3B. However, a common support member that supports the molds 100A and 100B can be used, and a single common conveyance unit 31 can be arranged for this support member. A case where the conveyance unit 31 is arranged independently for each of the conveying machines 3A and 3B enables handling cases where a movement strokes differ between the mold 100A and the mold 100B when conveying. For example, a case in which molds cannot be conveyed simultaneously since the widths of the molds (the width in the X direction) differ or the thickness of the molds (the width in the Y direction) differ.

The plurality rollers 32 configure a row of rollers arranged in the X-axis direction, where two rows are configured separated in the Y-axis direction. The plurality of rollers 32 rotate around the axis of revolution in the Z-axis direction, and guide movement in the X-axis direction of the mold 100A/100B contacting the side surfaces of the mold 100A/100B (the side surfaces of the clamping plates 101a and 102a) and supporting the mold 100A/100B from the side. The plurality rollers 33 configure a row of rollers arranged in the X-axis direction, where two rows are configured separated in the Y-axis direction. The plurality of rollers 33 rotate around the axis of revolution in the Y direction, and cause movement in the X direction of the mold 100A/100B to be smooth, supporting the bottom surfaces of the mold 100A/100B (the bottom surfaces of the clamping plates 101a and 102a) and supporting the mold 100A/100B from below.

The control apparatus 4 includes a controller 41 for controlling the injection molding machine 2, a controller 42A for controlling the conveying machine 3A, and a controller 42B for controlling the conveying machine 3B. Each of the controllers 41, 42A and 42B includes, for example, a processor such as a CPU, a RAM, a ROM, a storage device such as a hard disk, and interfaces connected to sensors or actuators (not illustrated). The processor executes programs stored in the storage device. An example of a program (control) that the controller 41 executes is described below. The controller 41 is communicably connected with the controllers 42A and 42B, and provides instructions related to the conveyance of the mold 100A/100B to the controllers 42A and 42B. The controllers 42A and 42B, if loading and unloading of the mold 100A/100B terminates, transmit a signal for operation completion to the controller 41. In addition, the controllers 42A and 42B transmit an emergency stop signal at a time of an abnormal occurrence to the controller 41.

A controller is arranged for each of the injection molding machine 2, the conveying machine 3A, and the conveying machine 3B, but one controller can control all three machines. The conveying machine 3A and the conveying machine 3B can be controlled by a single controller for more reliable and collaborative operation.

The injection molding machine 2 includes an injecting apparatus 5, a clamping apparatus 6, and a take-out robot 7 for ejecting a molded part. The injecting apparatus 5 and the clamping apparatus 6 are arranged on a frame 10 in the Y-axis direction.

The injecting apparatus 5 includes an injection cylinder 51 that is arranged to extend in the Y-axis direction. The injection cylinder 51 includes a heating device (not illustrated) such as a band heater, and melts a resin introduced from a hopper 53. A screw 51a is integrated into the injection cylinder 51, and by rotation of the screw 51a, plasticizing and measuring the resin introduced into the injection cylinder 51 are performed, and by movement in the axial direction (Y-axis direction) of the screw 51a, it is possible to inject a molten resin from an injection nozzle 52.

In FIG. 2, an example of a shut-off nozzle as the nozzle 52 is illustrated. For an opening/closing mechanism 56 of FIG. 2, a pin 56a for opening/closing the discharge port 52a is arranged. The pin 56a is connected with an actuator (a cylinder) 56c via a link 56b, and by the operation of the actuator 56c the discharge port 52a is opened and closed.

The injection cylinder 51 is supported by a driving unit 54. In the driving unit 54, a motor for plasticizing and measuring the resin by rotationally drive the screw 51a, and a motor for driving the screw 51a to move forward/backward in the axial direction are arranged. The driving unit 54 can move forward/backward in the Y-axis direction along a rail 12 on the frame 10, and in the driving unit 54, an actuator (for example, an electrically driven cylinder) 55 for causing the injecting apparatus 5 to move forward/backward in the Y-axis direction is arranged.

The clamping apparatus 6 performs a clamping and opening and closing of the molds 100A/100B. In the clamping apparatus 6, the following are arranged in order in the Y-axis direction: the fixed platen 61, a movable platen 62, and a movable platen 63. Through platens 61 to 63, a plurality of tie-bars 64 pass. Each of the tie-bars 64 is an axis that extends in the Y-axis direction, one end of which is fixed to the fixed platen 61. Each of the tie-bars 64 is inserted into a respective through hole formed in the movable platen 62. The other end of each of the tie-bars 64 is fixed to the movable platen 63 through an adjusting mechanism 67. The movable platens 62 and 63 can move in the Y-axis direction along a rail 13 on the frame 10, and the fixed platen 61 is fixed to the frame 10.

A toggle mechanism 65 is arranged between the movable platen 62 and the movable platen 63. The toggle mechanism 65 causes the movable platen 62 to move forward/backward in the Y-axis direction in relation to the movable platen 63 (in other words, in relation to the fixed platen 61). The toggle mechanism 65 includes links 65a to 65c. The link 65a is connected rotatably to the movable platen 62. The link 65b is pivotably connected to the movable platen 63. The link 65a and the link 65b are pivotably connected to each other. The link 65c and the link 65b are pivotably connected to each other. The link 65c is pivotably connected to an arm 66c.

The arm 66c is fixed on a ball nut 66b. The ball nut 66b engages a ball screw shaft 66a that extends in the Y-axis direction, and moves forward/backward in the Y-axis direction by rotation of the ball screw shaft 66a. The ball screw shaft 66a is supported such that it is free to rotate by the movable platen 63, and a motor 66 is supported by the movable platen 63. The motor 66 rotationally drives the ball screw shaft 66a while the rotation amount of the motor 66 is detected. Driving the motor 66 while detecting the rotation amount of the motor 66 enables clamping, opening, and closing of the mold 100A/100B.

The injection molding machine 2 includes sensors 68 for measuring a clamping force, where each sensor 68 is, for example, a strain gauge provided on the tie-bar 64, and calculates a clamping force by detecting a distortion of the tie-bar 64.

The adjusting mechanism 67 includes nuts 67b supported to freely rotate on the movable platen 63, motors 67a as driving sources, and transfer mechanisms for transferring the driving force of the motors 67a to the nuts 67b. Each of the tie-bars 64 passes through a hole formed in the movable platen 63, and engages with the nut 67b. By causing the nuts 67b to rotate, the engagement positions in the Y-axis direction between the nuts 67b and the tie-bars 64 change. That is, the position at which the movable platen 63 is fixed in relation to the tie-bar 64 changes. With this, it is possible to cause a space between the movable platen 63 and the fixed platen 61 to change, and thereby it is possible to adjust a clamping force or the like.

The molding operation position 11 is a region between the fixed platen 61 and the movable platen 62.

The mold 100A/100B introduced into the molding operation position 11 are sandwiched between the fixed platen 61 and the movable platen 62 and thereby clamped. Opening and closing in based on movement of the movable mold 102 by movement of the movable platen 62 is performed.

The take-out robot 7 includes a rail 71 that extends in the X-axis direction, and a movable rail 72 that can move in the X-axis direction on the rail 71. The movable rail 72 is arranged to extend in the Y-axis direction, and a slider 73 is arranged on the movable rail 72. The slider 73 moves in the Y-axis direction guided by the movable rail 72, and moves up and down an elevating shaft 73a in the Z-axis direction. On a lower end of the elevating shaft 73a, a vacuum head 74 is arranged, and on the vacuum head 74, a chuck plate 75 specialized to a molded part is mounted.

The take-out robot 7, after opening, moves the vacuum head 74 between the fixed mold 101 and the movable mold 102 as illustrated by broken lines in FIG. 2 by the rail 71, the movable rail 7, and the slider 73, sticks to the molded part, and conveys it outside the mold 100A/100B.

Capturing apparatus 76 is located above the fixed platen 61. The capturing apparatus 76 captures the molded part in a state where the vacuum head 74 holds the molded part to enable checking of the molded part.

Figure 3:
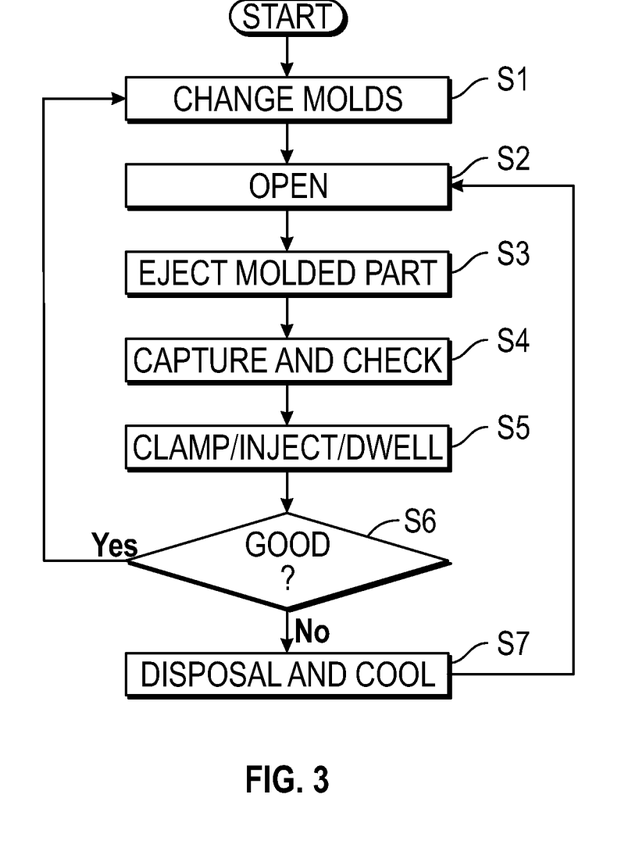
FIG. 3 illustrates a process of an operation of an injection molding system.

FIG. 3 illustrates a flowchart of a processing that the controller 41 executes. At the time execution of this flowchart begins, one of the molds 100A and the mold 100B is cooled on its respective conveying machine, and the other mold is in the dwelling process after injection in the injection molding machine 2.

In S1, the mold 100A/100B in the injection molding machine 2 and the mold 100A/100B on the conveying machine 3A/3B are changed (alternated).

The mold 100A/100B conveyed into the injection molding machine 2 in step 1 was previously cooled outside the injection molding machine.

In S2, the mold 100A/100B in the injection molding machine 2 is opened.

In S3, the take-out robot 7 removes (ejects) the molded part from the opened mold 100A/100B.

In S4, the capturing apparatus 76 captures an image of the molded part held by the take-out robot 7 and the molded part is checked. In a case where the timeframe analyze the captured image is an extended period, this process can be performed in parallel with the process of step 5.

In S5, a series of processes of clamping, injection into the mold 100A/100B, and dwelling is performed.

In S6, a determination, based on a result of checking the molded part, whether the molded part is considered acceptable or non-acceptable is made. In the present embodiment, the molded part is checked with respect to the surface condition and the shape of the molded part based on the captured image. The molded part can be checked with respect to the color of the molded part based on the captured image.

If the molded part is determined to be acceptable, the process returns to S1 and the molds 100A and 100B are changed.

If the molded part is determined to be non-acceptable, the molds 100A and 100B are not changed and the process proceeds to S7. In S7, the process waits until molding material injected into the mold in S5 is sufficiently cooled. Once sufficiently cooled, the non-acceptable part is disposed of by moving it to a different location from the accepted part. The process then proceeds to S1, where the molds 100A and 100B are changed.

As described above, n the flowchart of FIG. 3, if the molded part is acceptable, the molds 100A and 100B are changed and the process is repeated. If the molded part is non-acceptable, the molds 100A and 100B are not changed, and the opening and the ejection process are performed for the same mold 100A/100B. This enables a quick re-manufacturing of the molded part when the ejected molded part is non-acceptable. This process also enables maintaining the order of the ejected part when needed, such as when molded part A and molded part B need to be alternately packed in a storage container.

Figure 4:
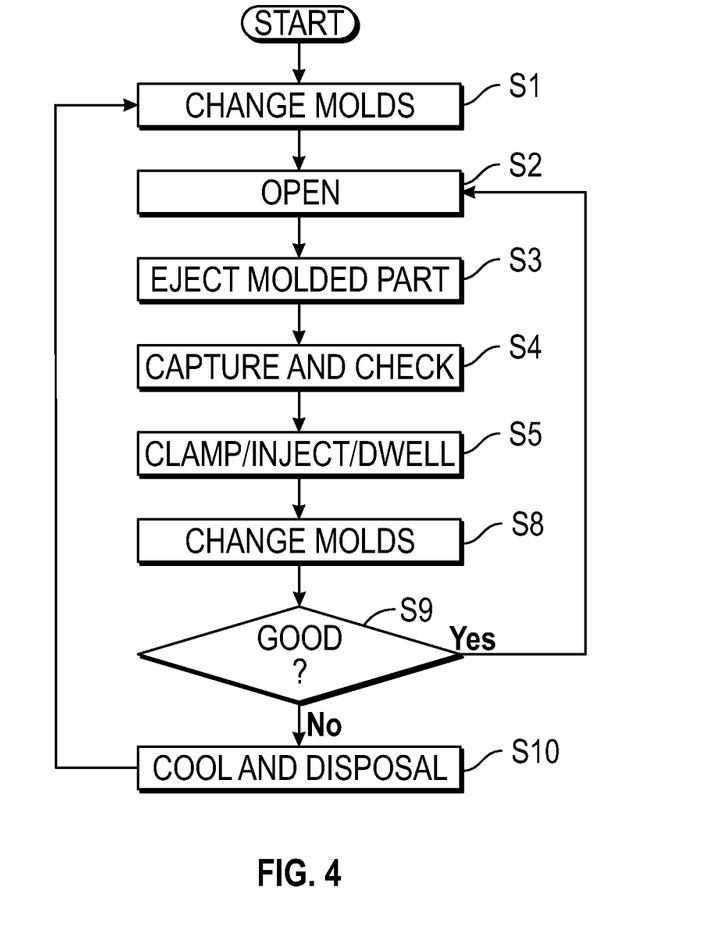
FIG. 4 illustrates a process of an operation of an injection molding system.

FIG. 4 illustrates a flowchart of a processing that the controller 41 executes. S1 to S5 in FIG. 4 are identical to S1 to S5 in FIG. 3 and their descriptions are omitted herein.

In S8, the molds 100A and 100B are changed after the dwelling process.

In S9, a determination, based on a result of checking the molded part, whether the molded part is considered acceptable or non-acceptable is made. If the molded part is determined to be acceptable, the returns to S2.

If the molded part is determined to be non-acceptable, the flow proceeds to S10. In S10, the process waits until molding material injected into the mold in S5 is sufficiently cooled. Once sufficiently cooled, the non-acceptable part is disposed of by moving it to a different location from the accepted part. The process then proceeds to S1, where the molds 100A and 100B are changed. This enables a quick re-manufacturing of the molded part when the ejected molded part is non-acceptable.

As described above, in the flowchart of FIG. 4, the molds 100A and 100B are changed before it is determined whether the molded part is acceptable, and it is determined whether the molded part is acceptable before the changed mold 100A/100B is opened. In a case where the molded part is acceptable, it is possible to reduce or remove the time for waiting until it is determined whether the molded part is acceptable. In a case where the molded part is non-acceptable, the molds 100A and 100B are changed again, and the mold 100A/100B that was used when the non-acceptable part was manufactured is returned to the injection molding machine 2. Since rate of manufacturing acceptable molded parts is greater than the possibility that the molded part is non-acceptable, time required for executing the entire process can be reduced.

In the flowchart in FIG. 4, the checking process is performed in S4, and the determination process is performed in S9. In another exemplary embodiment, while the checking process is started in S4, the checking process and the determination process can be performed in parallel with the clamping, injection, dwelling process in S5 and the changing process in S8. In this case, the determination process in S9 can be performed between S5 to S8.

If the determination process in S9 completes before the process in S5 completes or just after the process in S5 completes, the same process illustrated in FIG. 3 is performed. That is, the changing process in S8 is omitted, and the molds 100A and 100B are changed in S1 in a case where the molded part is determined to be acceptable in S9, and the process in S10 and the process in S2 are performed in a case where the molded part is determined to be non-acceptable in S9.

As described above, the present embodiment can switch between the process in FIG. 3 and the process in FIG. 4 based on the time for the capturing and checking processes. The process of FIG. 4 provides an enhancement to the process of FIG. 3 in, for example, a case where the timeframe to execute the image processing and analyzing of captured image is lengthy, and the determination process is not finished after the dwelling process completes.

Figure 5:
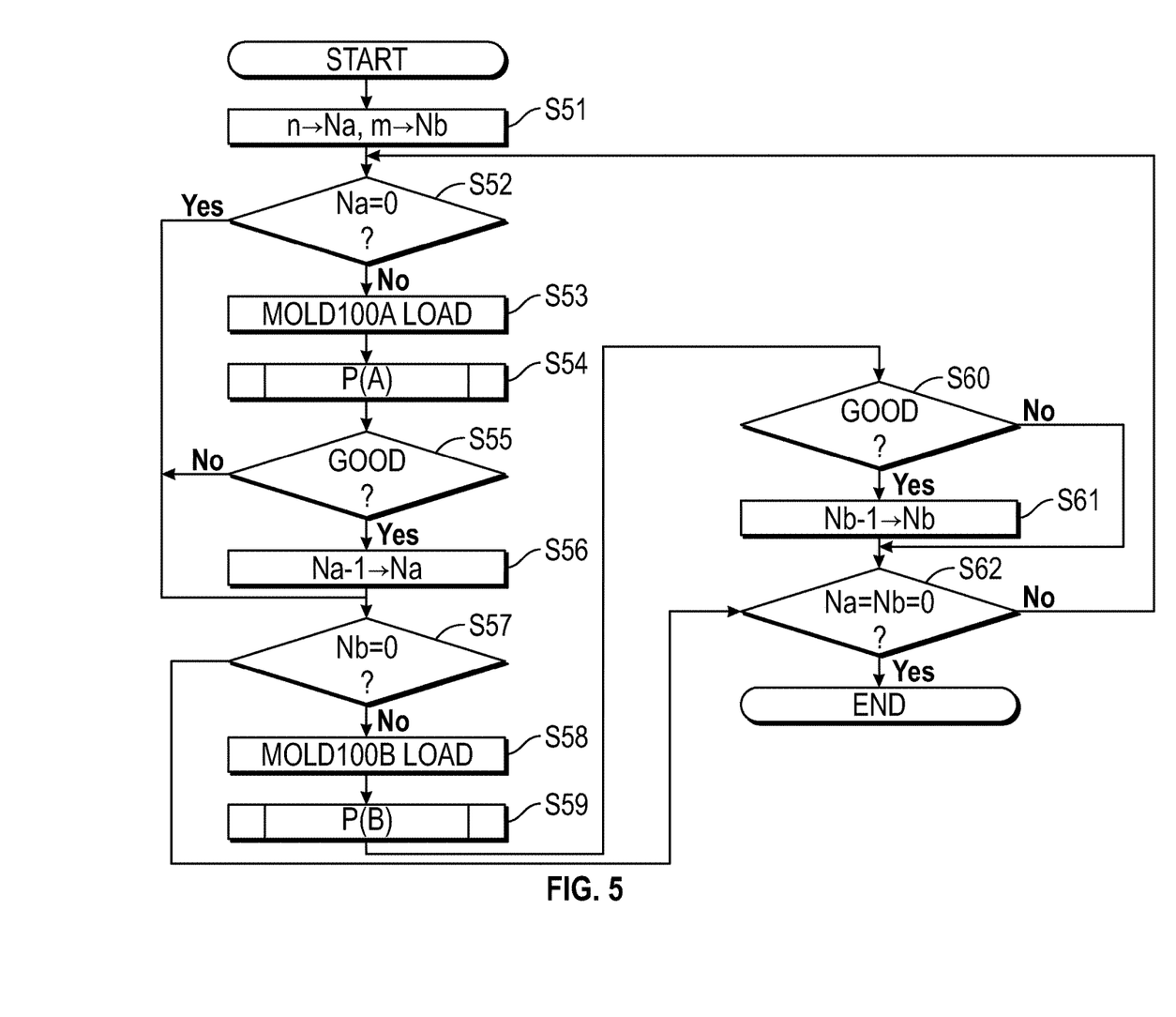
FIG. 5 illustrates an operation of an injection molding system.

FIG. 5 illustrates a flowchart of a processing that the controller 41 executes. More specifically, the controller 41 manages the number of the molded parts manufactured by both the mold 100A and the mold 100B, and updates the scheduled number of the molded part based on manufacture of a non-acceptable part.

At the time execution of this flowchart begins, one of the molds 100A and the mold 100B is cooled on its conveying machine, and the other mold is in the dwelling process after injection in the injection molding machine 2.

In S51, the controller 41 sets the number of the molded part manufactured by each of the mold 100A and mold 100B. In one exemplary embodiment, the controller 41 performs this process in response to an input by a user. The controller 41 assigns the scheduled number "n" to the variable Na that indicates the residual number of the molded part manufactured by the mold 100A. The controller 41 assigns the scheduled number "m" to the variable Nb that indicates the residual number of the molded part manufactured by the mold 100B.

In S52, it is determined whether the residual number Na is equal to 0. If Na is equal to 0, the process proceeds to S57. If Na is not equal to 0, the process proceeds to S53. In S53, the mold 100A is conveyed into the injection molding machine 2. If the mold 100A is already in the injection molding machine 2 at this time, the controller 41 does carry out any processing.

Figure 6:
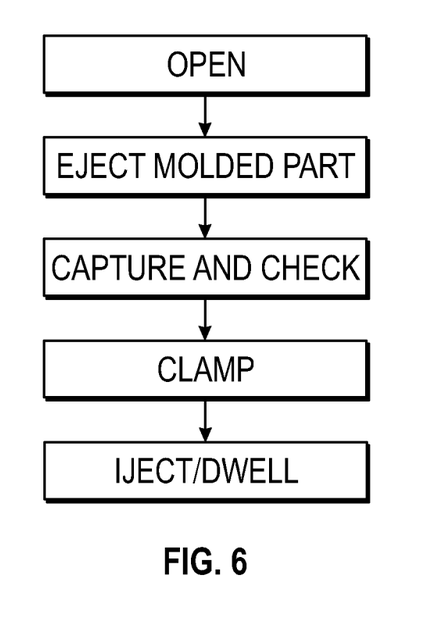
FIG. 6 illustrates a basic molding process.

In S54, basic molding process P illustrated in FIG. 6 is performed with the mold 100A.

The basic molding process P is a standard process for a mold conveyed into the injection molding machine 2.

In the present embodiment, the basic molding process includes opening the mold, ejection of the molded part, capturing and checking the molded part, clamping, injection, and dwelling. However, the basic molding process can change based on the molded part and the molding process adopted by the injection molding machine 2. In the checking process in the basic molding process P, the take-out robot 7 maintains holding the molded part. In another exemplary embodiment, a table and the checking apparatus can be provided near the injection molding system 1, and the checking process can be performed on the table.

In S55, it is determined whether the molded part ejected in S54 is acceptable. If the molded part is acceptable, the process proceeds to S56. In S56, the residual number Na for the mold 100A decreases by one.

If the molded part is non-acceptable, the process proceeds to S57, and the residual number Na does not decrease. That is, the molded part will be re-manufactured as the same number of the non-acceptable part.

In S57, it is determined whether the residual number Nb is equal to 0. If Nb is equal to 0, the process proceeds to S62. If Na is not equal to 0, the process proceeds to S58. In S58, the mold 100B is conveyed into the injection molding machine 2. If the mold 100B is already in the injection molding machine 2 at this time, the controller 41 does not carry out a processing.

In S59, the basic molding process P illustrated in FIG. 6 is performed with the mold 100B.

In S60, it is determined whether the molded part ejected in S59 is acceptable. If the molded part is acceptable, the processing proceeds to S61. In S61, the residual number Nb for the mold 100B decreases by one.

If the molded part is non-acceptable, the process proceeds to S62, so the residual number Nb does not decrease. That is, the molded part will be re-manufactured as the same number of the non-acceptable part.

In S62, it is determined whether both the residual number Na and the residual number Nb are equal to 0. If Na and Nb are equal to 0, the process ends. If either Na or Nb is not equal to 0, the process returns to S52.

The process of FIG. 5 is repeated until Na and Nb are equal to 0.

As described above, in the present embodiment, it is possible to change the preset manufacturing number of the molded part based on the result of the checking apparatus in response to that the molded part being determined as non-acceptable. The above-described embodiment also provides an efficient manufacturing method including a checking process in the manufacturing process for performing injection molding while changing multiple molds.

In another exemplary embodiment, a checking process for the molded part is included in an injection molding that performs assembling in the mold or insert molding while changing multiple molds. A configuration and process flow for the assembling in the mold is described below.

Figure 7:
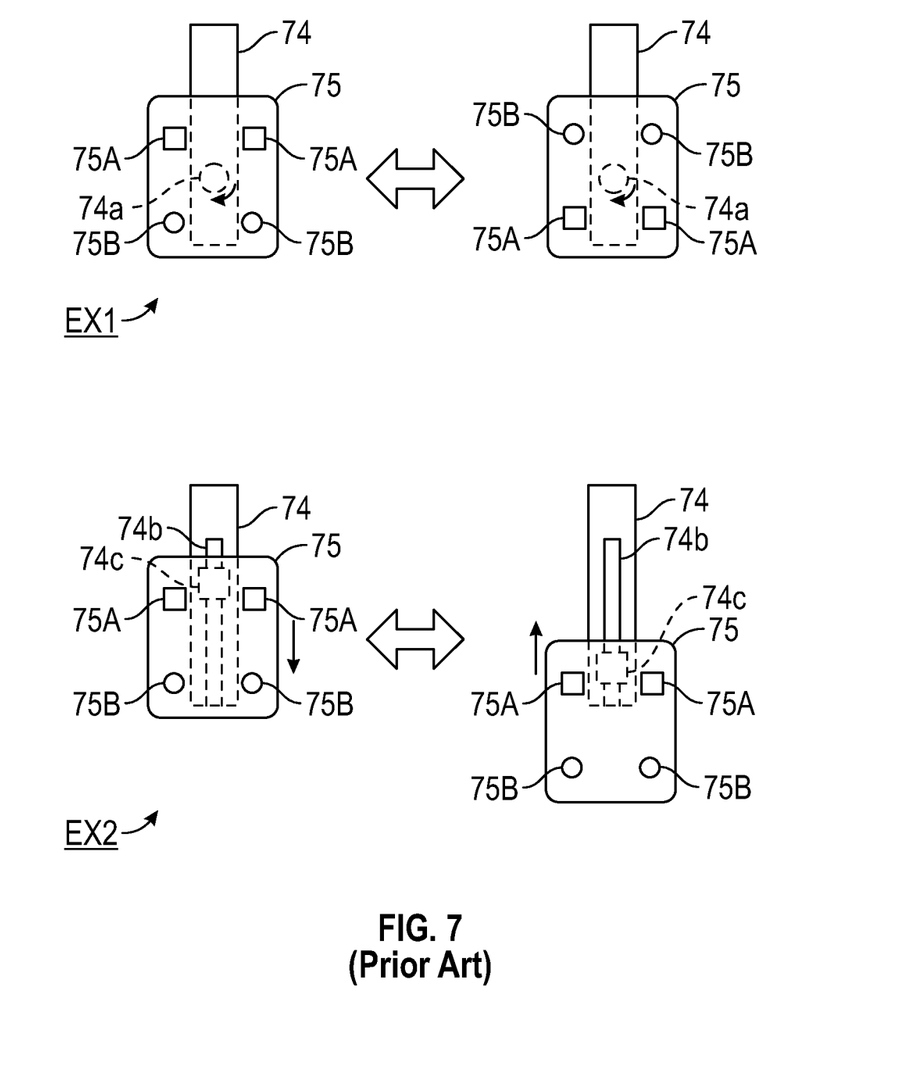
FIG. 7 illustrates a chuck plate.

FIG. 7 is being provided herein for information purposes only. EX1 of FIG. 7 indicates an example of the chuck plate 75. The chuck plate 75 includes a holding portion 75A and a holding portion 75B. The vacuum head 74 causes the chuck plate 75 to rotate around an axis 74a, and causes the chuck plate 75 to be displaced so that the positions of the holding portion 75A and the holding portion 75B change. This provides for switching the holding portion facing the molded part, handling different molded parts in a short time without replacing the chuck plate 75. EX2 of FIG. 6 illustrates another example of the chuck plate 75. The chuck plate 75 includes a holding portion 75A and the holding portion 75B. The vacuum head 74 includes a rail 74b and a slider 74c that moves along the rail 74b, and the chuck plate 75 is arranged on the slider 74c. Moving the slider 74c results in the chuck plate 75 being displaced to change the positions of the holding portion 75A and the holding portion 75B. This provides for switching the holding portion facing the molded part handling different molded parts in a short time without replacing the chuck plate 75.

Figure 9:
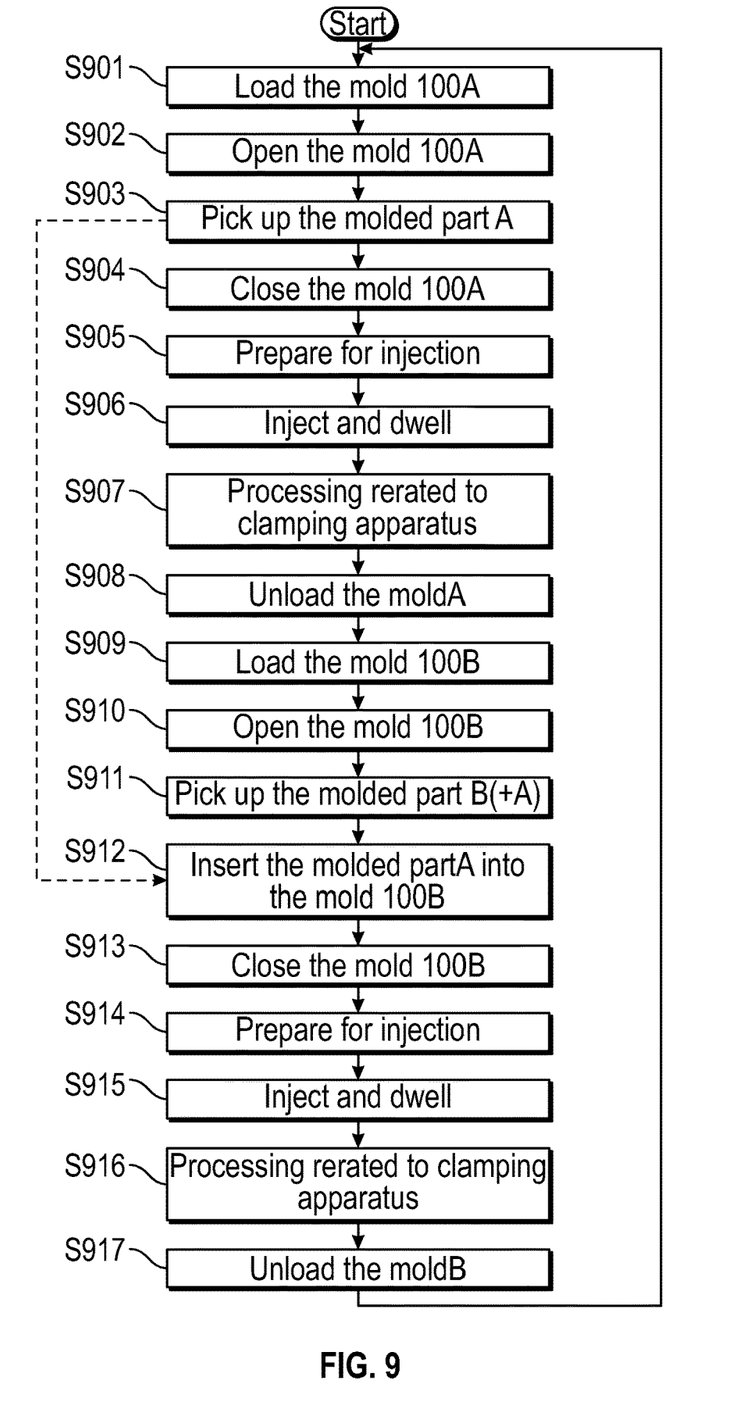
FIG. 9 illustrates a process of injection molding.

FIG. 9 is a flowchart illustrating an example of a control method of the injection molding system 1 executed by the controller 41. In the following example, a case in which a molding operation is performed while alternating the molds 100A and 100B in the following manner: molding using the mold 100A→molding using the mold 100B→molding using the mold 100A, etc., is envisioned. However, a molded part A molded in the mold 100A is placed in the mold 100B when the mold 100B is open. Then, a resin is injected in the mold 100B containing the molded part A, and a molded part B united with the molded part A is manufactured.

At the beginning of this processing flow, the mold 100B with resin injected has been unloaded from the injection molding machine 2 to the conveyance machine 3B. The following description describes the processes that follow this step. In step S1 of FIG. 5, the cooled mold 100A is loaded into the injection molding machine 2. The mold A includes the molded part A that was made from the resin injected in the previous cycle and then hardened in the cooling process. In step S2, the motor 66 is driven to move the movable platen 62 away from the stationary platen 61. The stationary mold 101 is fixed to the stationary platen 61 by the fixing mechanisms 610, and the movable mold 102 is fixed to the movable platen 62 by the fixing mechanisms 610. Thus, the movable mold 102 separates from the stationary mold 101 and the mold 100A is opened.

In step S3, the take-out robot 7 drives the holding portion 75A to remove the molded part A, remaining on the side of the movable mold 102 of the mold 100A. The molded part A that is removed continues to be held by the holding portion 75A until the process of step S12.

In step S4, the clamping device 6 drives the motor 66 to drive the toggle mechanism 65 to perform clamping of the mold 100A with the stationary platen 61 and the movable platen 62.

In step S5, the preparation for injection to the mold 100 A is performed by the injecting machine 5. The injecting machine 5 drives the actuator 55 to move the injection machine 5 to move the nozzle 52 such that it contacts the mold 100A.

In step S6, injection and dwelling of molten resin is performed. The injection machine 5 is driven to fill molten resin into a cavity in the mold 100A from the nozzle 52, and to press the resin into the mold 100A at a high pressure in order to compensate for a volume decrease due to resin solidifying. The actual clamping force is measured by the sensor 68 during the processing of step S6. During molding, the mold 100A thermally expands due to the temperature of the mold 100A gradually rising. There are cases where a difference arises in the initial clamping force and the clamping force after a period of time has passed. Accordingly, it is possible to correct the clamping force at the time of the next clamping based on a result of measurement by the sensors 68.

The adjustment of the clamping force is performed by an adjustment of the position of the movable platen 63 in relation to the tie-bar 64 by driving the motor 67. This enables enhance precision of the clamping force by adjusting the clamping force by correcting the initial value of the position of the movable platen 63 in relation to the tie-bars 64 based on the result of measurement by the sensors 68. The adjustment of the position of the movable platen 63 in relation to the tie-bars 64 can be performed at any timing (for example, step S6, step S7, steps S13-S15 in the flowchart of FIG. 5).

In step S7, processing related to the clamping device 6 is performed. First, locking of the mold 100A by the fixation mechanisms 610 is released. The motor 66 is driven to drive the toggle mechanism 65. This results in removal of the clamping force, the movable platen 62 separates slightly in relation to the stationary platen 61, and a space in which it is possible to alternate the molds 100A and 100B is formed.

In step S8, the mold 100A is unloaded or ejected from the molding operation position 11 to the conveying machine 3A. After the mold 100A is ejected from the molding operation position 11, the mold 100A is cooled to the appropriate temperature during for predetermined time period. A mold typically includes a channel running inside the mold, a temperature controller is connected, via a hose, to the interface of the channel formed on a surface of the mold, while the mold is prepared for injection molding. The fluid at a certain temperature flows from the temperature controller inside the mold, to keep the mold at a certain temperature. During the injection molding processes, including the cooling process, fluid is usually always running inside the mold.

Typically, after step S8, the mold 100A is still heated up from the melted resin injected into the mold 100A. In the cooling process by the fluid from the temperature controller, the temperature is dropped to a predefined temperature, for example 60 degrees Celsius. The cooling process continues until a predetermined time period passes from the start of the cooling process.

In some injection molding processes like heat and cool molding, the cooling process includes a dedicated temperature controller to cool down a mold to a certain temperature, which is different from a temperature at which a mold receives the melted resin from an injecting machine.

In step S9, the mold 100B is loaded from the conveying machine 3B to the molding operation position 11. In step S10, the movable platen 62 is separated from the fixed platen 61 by driving the motor 66. The stationary mold 101 is fixed to the stationary platen 61 by the fixing mechanisms 610, and the movable mold 102 is fixed to the movable platen 62 by the fixing mechanisms 610. Therefore the movable mold 102 separates from the stationary mold 101 and the mold 100B is opened against the force of the self-closing unit 103. In step S11, the molded part B, which is united with molded part A, remaining on the side of the movable mold 102 of the mold 100B is removed by driving the take-out robot 7 and using the holding portion 75B is conveyed outside the injection molding machine 2.

In step S12, the molded part A being held by the holding portion 75A is placed in the metal mold B. In step S13, clamping of the mold 100B is performed. In step S14, preparation for injection to the mold 100B is performed by driving the actuator 55 to move the injection machine 5. This causes the nozzle 52 to contact the mold 100B.

In step S15, injection and dwelling of molten resin is performed. In step S16, processing related to the clamping device 6 is performed, which is the same process as in step S7. In step S17, the mold 100B is unloaded from the molding operation position 11 to the conveying machine 3B.

As described above, in the present embodiment, cooling of the mold 100A/100B is performed on the conveying machines 3A or 3B outside the injection molding machine 2. Also, during cooling of one of the molds 100A or 100B, each process of molded part ejection→clamping→injection/dwelling is performed by the injection molding machine 2 for the other of the mold 100A or 100B. Since opening and molded part ejection are performed by the injection molding machine 2, the conveying machines 3A and 3B do not need to include a function for opening and a function for molded part ejection.

Accordingly, it is possible to manufacture the molded part B united with molded part A while alternating the multiple molds 100A and 100B by one injection molding machine 2 while avoiding cost increases to the injection molding system 1. Because the injection molding system 2 molds a molded part B following the molding of a molded part A, it is not necessary to manufacture a large quantity of molded part A beforehand. Thus, it is possible to decrease the risk of storing excess inventory of molded part A.

Figure 8:
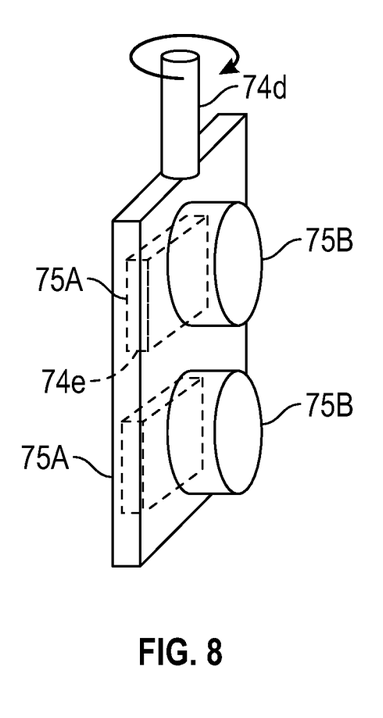
FIG. 8 illustrates a chuck plate.

FIG. 8 is an illustrative view of a chuck plate of another exemplary embodiment. FIG. 8 illustrates the chuck plate 74e connected to the tip of the axis 74d. The chuck plate 74e includes several holding portions 75A on one surface and several holding portions 75B on another surface. It is possible to switch the holding portion facing the molded part by rotating the chuck plate 74e around an axis 74d. The rotation angle is not limited to 180 degree. Any angle that enables the holding portion to properly catch and hold the molded part is applicable.

In case it is necessary to sufficiently cool down the molded part before it is placed in the mold 100B, the molded part A can be cooled on a table during one or more cycles of changing the molds 100A and 100B have passed. In this case, the molded parts A can be placed on the table for a time period longer than the number of cycles necessary to cool them. This enables using a molded part A that was molded one or more exchange cycles ago as the molded part to place in the mold 100B.

A sensor can be installed in the mold 100A/100B to enable detecting that the molded part A was placed in the mold 100B. The sensor can be placed in the mold 100B or can be attached at various positions in the injection molding machine 2. A pressure sensor or optical sensor can be used as the sensor.

An image of the placement condition can be obtained with a camera installed in the vicinity of the molding operation position 11, where placement can be determined based on the obtained image.

A table can be prepared to adjust a holding orientation of the molded part A held by the take-out robot 7. Repositioning of the molded part A can also occur on the table. In this case, a configuration can be created to link a sensor installed in the vicinity of the table or on the take-out robot 7 to change the hold to an orientation such that the molded part is placed in the mold 100B.

In a case where the molded part A is non-acceptable, the molded part B including the molded part A does not become acceptable. Thus, checking (inspecting) whether the molded part A is acceptable before the molded part A is placed in the mold 100B should be conducted.

In the checking process (inspection process), for example, a camera located in the injection molding machine 2 captures an appearance image of the molded part. The molded part is checked with respect to the surface condition and the shape of the molded part based on the captured image. The molded part can be checked with respect to the color of the molded part based on the captured image. A capturing device that captures an internal structure of the molded part using radiation, such as X-ray, can be used in the checking process. In a case where the checking process for the molded part B is performed outside the injection molding machine 2, the checking process for the molded part A performed in the injection molding machine 2 may be the only appearance inspection.

In the checking process, the molded part A is removed by the take-out robot 7, one or more cameras capture an appearance image in a state where the molded part A is held by the take-out robot 7, the captured image is analyzed, and a result indicating whether the molded part A acceptable is output. The captured image can be analyzed by specialized hardware.

The molded part A removed by the take-out robot 7 can be placed at a predetermined position outside the injection molding machine 2, and the checking process for the molded part A can be performed outside the injection molding machine 2. In this case, the take-out robot 7 does not keep holding the molded part A during a period from when the take-out robot 7 removes the molded part A from the mold 100A to when the take-out robot 7 places the molded part A in the mold 100B.

Several options are available after the molded part is determined to be non-acceptable. In a first option, the mold 100A is not moved from the molding operation position 11 in the injection molding machine 2, and the injection molding using the mold 100A is re-performed. In a case where the mold 100A has previously been moved from the injection molding machine 2 before the checking process is performed, the mold 100A is moved to the injection molding machine 2 again, and the injection molding using the mold 100A is re-performed again. After that, the molded part A is re-checked. If the molded part A is determined as acceptable, the molded part A is placed in the mold 100B. If the molded part A is determined as acceptable, the mold 100A is moved from the injection molding machine 2 and the mold 100B is moved into the injection molding machine 2.

In a second option, another acceptable part is prepared outside the injection molding machine 2 in advance, the prepared molded part A is held by the take-out robot 7 and used instead of the non-acceptable part. In this case, based on the determination that indicates that the molded part A is non-acceptable, the control device 4 controls the take-out robot 7 so that the non-acceptable part is removed from the take-out robot 7 and the non-acceptable part is disposed of. The prepared molded part A is held by the take-out robot 7 and placed in the mold 100B. If the molded part A is determined as acceptable, the molded part A that was is just removed by the take-out robot 7 from the mold 100A is placed in the mold 100B.

In a third option, the take-out robot 7 places the molded part A at a predetermined position outside the injection molding machine 2. In this case, after placing the molded part A at the predetermined position, the take-out robot 7 holds another molded part A determined as acceptable and places it in the mold 100B. This flow is effective in a case where a time required to check the molded part A is relatively long.

In the second option, it is preferable to produce some molded parts A in advance. That is, the mold 100A is placed at the molding operation position 11 and the injection molding is performed until a predetermined number, e.g. 10 of the acceptable molded part A is produced. The injection molding machine 2 operates in a mode that the injection molding using only the mold 100A is performed. In a case where the predetermined number of the acceptable molded part A is produced, the injection molding machine 2 enters a mode that the injection molding alternately uses the mold 100A and the mold 100B. The mode that the injection molding using only the mold 100A is performed can be implemented in the third option.

In the injection molding process after the molded part A is determined as defective in the first option, and the injection molding process for producing the predetermined number of the molded parts A in advance, it is not necessary to cool the mold 100A at a position other than the molding operation position 11. In other words, it is not necessary to cool the mold 100A in a state where the mold 100A is moved out of the injection molding machine 2. However, there is a difference between a pressure applied to the mold 100A/100B in a case where the mold is cooled on the conveying machine 3A/3B and a pressure applied to the mold 100A/100B in a case where the mold 100A/100B is cooled at the molding operation position 11 in the injection molding machine 2, so the quality of the mold 100A/100B can be different in each of the cases.

In the above injection molding processes, the mold 100A can be cooled in the state where the mold 100A is moved from the molding operation position 11. The mold 100A can be cooled in the state where the mold 100A is at the molding operation position 11, and the fixed platen 61 and moveable platen 62 can be separated from the mold 100A. This makes the pressure applied to the mold 100A similar to that in the state where the mold 100A is cooled on the conveying machine 3A.

In the above-described embodiments, clamping, injection/dwelling, opening, and ejection are performed in the state where the mold 100A/100B is at the molding operation position 11, but this is not seen to be limiting. It is not necessary to perform all processes at the molding operation position 11. Part of the processes can be performed at a position different from the molding operation position 11.

In the above-described embodiments, the cooling process is performed in the state where the mold 100A/100B is on the conveying machine 3A/3B, but this is no seen to be limiting. It is not necessary to perform the cooling process on the conveying machines 3A and 3B. The cooling process can be performed at a position where the mold 100A/100B does not contact the fixed platen 61 and the movable platen 62. For example, the cooling process can be performed in a state where a part of the mold 100A/100B is in the injection molding machine 2 and another part of the mold is outside the injection molding machine 2. In a case where a configuration that a part of either of the conveying machines 3A and 3B is located in the injection molding machine 2 is adopted, the cooling process can be performed in a state where a part of the mold 100A/100B is in the injection molding machine 2 and another part of the mold 100A/100B is on either of the conveying machines 3A/3B.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "includes", "including," and "containing" are to be construed as open-ended terms (i.e., meaning "including, but not limited to,") unless otherwise noted. Specifically, these terms, when used in the present specification, specify the presence of stated features, integers, steps, operations, elements, and/or components, but do not preclude the presence or addition of one or more other features, integers, steps, operations, elements, components, and/or groups thereof not explicitly stated. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

It will be appreciated that the methods and compositions of the instant disclosure can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Combinations of any exemplary embodiments disclosed above are also included as embodiments of the present disclosure. While the above-described exemplary embodiments discuss illustrative embodiments, these embodiments are not seen to be limiting.

What is claimed is:

1. A method for manufacturing a molded part by an injection molding machine while changing between multiple molds, the method comprising:
    a first ejecting step of opening a first mold in the injection molding machine and ejecting the molded part from the first mold;
    a checking step of checking the molded part, ejected in the first ejecting step, to determine if the molded part is an acceptable part;
    a first injecting step of closing the first mold and performing injection into the first mold; and
    a second ejecting step,
    wherein, in a case where the molded part ejected in the first ejecting step is determined to be an acceptable part, the second ejecting step includes changing the first mold in the injection molding machine to a second mold, a second injecting step of closing the second mold and performing injection into the second mold, and ejecting another molded part from the second mold after the first injecting step; and
    wherein, in a case where the molded part ejected in the first ejecting step is determined to be a non-acceptable part, the second ejecting step does not include changing the first mold to the second mold, and includes ejecting the molded part from the first mold.

2. The method according to claim 1, wherein a shape of the first mold is different from a shape of the second mold.

3. The method according to claim 1, wherein the checking step includes analyzing a captured image of the molded part.

4. The method according to claim 1, wherein the checking step is completed before start of changing from the first mold to the second mold.

5. The method according to claim 1, further comprising:
    a placing step of placing the molded part ejected from the first mold into a cavity in the second mold; and
    a second injecting step of closing the second mold into which the molded part is placed and performing injection into the second mold.

6. The method according to claim 5, wherein the placing step includes, in a case where the molded part ejected from the first mold is the non-acceptable part, the molded part different from the non-acceptable part, ejected from the first mold, and checked as the acceptable part is placed in the cavity in the second mold.

7. A method for manufacturing a molded part by an injection molding machine while alternating between multiple molds, the method comprising:
    a first ejecting step of opening a first mold in the injection molding machine and ejecting the molded part from the first mold;
    a checking step of checking the molded part, ejected in the first ejecting step, to determine if the molded part is an acceptable part;
    a first injecting step of closing the first mold and performing injection into the first mold;

a first changing step of changing the first mold in the injection molding machine to a second mold;

a second ejecting step of, in a case where the molded part ejected in the first ejecting step is an acceptable part, that includes a second injecting step of closing the second mold and performing injection into the second mold, and ejecting another molded part from the second mold after the first changing step; and a second changing step of, in a case where the molded part ejected in the first ejecting step is a non-acceptable part, not ejecting the another molded part from the second mold, and changing the second mold in the injection molding machine to the first mold.

8. The method according to claim 7, wherein a shape of the first mold is different from a shape of the second mold.

9. The method according to claim 7, wherein the checking step includes analyzing a captured image of the molded part.

10. The method according to claim 7, wherein the checking step is completed before start of changing from the first mold to the second mold.

11. The method according to claim 7, further comprising:
a placing step of placing the molded part ejected from the first mold into a cavity in the second mold; and
a second injecting step of closing the second mold into which the molded part is placed and performing injection into the second mold.

12. The method according to claim 11, wherein the placing step includes, in a case where the molded part ejected from the first mold is the non-acceptable part, the molded part different from the non-acceptable part, ejected from the first mold, and checked as the acceptable part is placed in the cavity in the second mold.

13. A method for manufacturing a molded part by an injection molding machine while changing between multiple molds, the method comprising:
a first injection step for injecting material into a first mold positioned at a molding operation position of the injection molding machine;
a first ejecting step for ejecting, from the first mold, a molded part created from the material injected in the first injecting step;
a second injection step for injecting material into the first mold;
a determination step for determining if the molded part ejected in the first ejecting step is a non-acceptable part;
a second ejecting step for ejecting from the first mold a molded part created from the material injected in the second injecting step;
a first changing step, performed after the determination step and before the second ejecting step, for conveying the first mold from the molding operation position and conveying a second mold into the molding operation position; and
a second changing step of, in a case where the molded part ejected in the first ejecting step is a non-acceptable part, not ejecting another molded part from the second mold, and changing the second mold in the injection molding machine to the first mold,
wherein the second mold is different from the first mold, and
wherein the injection molding machine comprises a camera and the determining in the determination step is performed via an image of the molded part captured by the camera.

* * * * *